(12) United States Patent
Rong et al.

(10) Patent No.: US 11,690,563 B2
(45) Date of Patent: Jul. 4, 2023

(54) METHODS AND SYSTEMS FOR REMOTE SLEEP MONITORING

(71) Applicant: ARIZONA BOARD OF REGENTS ON BEHALF OF ARIZONA STATE UNIVERSITY, Scottsdale, AZ (US)

(72) Inventors: Yu Rong, Tempe, AZ (US); Alex Chiriyath, Tempe, AZ (US); Arindam Dutta, Tempe, AZ (US); Daniel W. Bliss, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/772,844

(22) PCT Filed: Oct. 27, 2020

(86) PCT No.: PCT/US2020/057452
§ 371 (c)(1),
(2) Date: Apr. 28, 2022

(87) PCT Pub. No.: WO2021/086809
PCT Pub. Date: May 6, 2021

(65) Prior Publication Data
US 2023/0018038 A1 Jan. 19, 2023

Related U.S. Application Data

(60) Provisional application No. 62/926,717, filed on Oct. 28, 2019.

(51) Int. Cl.
*A61B 5/00* (2006.01)
*A61B 5/0205* (2006.01)
*A61B 5/05* (2021.01)

(52) U.S. Cl.
CPC .......... *A61B 5/4812* (2013.01); *A61B 5/0205* (2013.01); *A61B 5/05* (2013.01); *A61B 5/4818* (2013.01)

(58) Field of Classification Search
CPC ........ A61B 5/4812; A61B 5/0205; A61B 5/05
(Continued)

(56) References Cited

U.S. PATENT DOCUMENTS

| 4,860,014 A | 8/1989 | Shores et al. |
| 5,424,749 A | 6/1995 | Richmond |

(Continued)

FOREIGN PATENT DOCUMENTS

| CN | 106264501 A | 1/2017 |
| JP | 2022153626 A | 10/2022 |

(Continued)

OTHER PUBLICATIONS

Anderson, N. et al., "A 118-mW Pulse-Based Radar SoC in 55-nm CMOS for Non-Contact Human Vital Signs Detection," IEEE Journal of Solid-State Circuits, vol. 52, No. 12, Dec. 2017, IEEE, pp. 3421-3432.

(Continued)

*Primary Examiner* — John R Downey
(74) *Attorney, Agent, or Firm* — Withrow & Terranova, P.L.L.C.; Vincent K. Gustafson

(57) ABSTRACT

Methods and systems for remote sleep monitoring are provided. Such methods and systems provide non-contact sleep monitoring via remote sensing or radar sensors. In this regard, when processing backscattered radar signals from a sleeping subject on a normal mattress, a breathing motion magnification effect is observed from mattress surface displacement due to human respiratory activity. This undesirable motion artifact causes existing approaches for accurate heart-rate estimation to fail. Embodiments of the present (Continued)

disclosure use a novel active motion suppression technique to deal with this problem by intelligently selecting a slow-time series from multiple ranges and examining a corresponding phase difference. This approach facilitates improved sleep monitoring, where one or more subjects can be remotely monitored during an evaluation period (which corresponds to an expected sleep cycle).

14 Claims, 8 Drawing Sheets

(58) Field of Classification Search
USPC .......................................................... 600/301
See application file for complete search history.

(56) References Cited

U.S. PATENT DOCUMENTS

| | | | |
|---|---|---|---|
| 5,565,872 | A | 10/1996 | Prevatt et al. |
| 5,828,331 | A | 10/1998 | Harper |
| 6,026,340 | A | 2/2000 | Corrado et al. |
| 8,712,069 | B1 | 4/2014 | Murgia et al. |
| 9,164,167 | B2 | 10/2015 | Hyde et al. |
| 10,310,073 | B1* | 6/2019 | Santra ................ A61B 5/0816 |
| 2005/0168336 | A1 | 8/2005 | Donskoy et al. |
| 2006/0054438 | A1 | 3/2006 | Asaba et al. |
| 2006/0253278 | A1 | 11/2006 | Furst-Yust et al. |
| 2008/0077015 | A1 | 3/2008 | Boric-Lubecke et al. |
| 2008/0135762 | A1 | 6/2008 | Villanucci et al. |
| 2008/0151694 | A1 | 6/2008 | Slater |
| 2009/0203972 | A1 | 8/2009 | Heneghan et al. |
| 2010/0011845 | A1 | 1/2010 | Laughard, Jr. et al. |
| 2010/0152600 | A1 | 6/2010 | Droitcour et al. |
| 2010/0290063 | A1 | 11/2010 | Bakhtiari et al. |
| 2013/0053653 | A1 | 2/2013 | Cuddihy et al. |
| 2014/0194793 | A1 | 7/2014 | Nakata et al. |
| 2014/0212986 | A1 | 7/2014 | Angelescu et al. |
| 2015/0319540 | A1 | 11/2015 | Rubinstein et al. |
| 2016/0022204 | A1 | 1/2016 | Mostov |
| 2016/0089052 | A1 | 3/2016 | Cho et al. |
| 2018/0000408 | A1 | 1/2018 | Heinrich et al. |
| 2019/0059746 | A1* | 2/2019 | McMahon ............ G01S 13/18 |
| 2020/0196866 | A1 | 6/2020 | Chiou et al. |
| 2021/0093203 | A1* | 4/2021 | Zhong ................ A61B 5/0507 |
| 2021/0353156 | A1 | 11/2021 | Rong et al. |
| 2022/0142478 | A1* | 5/2022 | Bliss .................... A61B 5/16 |
| 2022/0373646 | A1* | 11/2022 | Nguyen ................ G01S 13/88 |
| 2023/0000396 | A1* | 1/2023 | Coffey ................ A61B 5/1117 |

FOREIGN PATENT DOCUMENTS

| | | |
|---|---|---|
| WO | 0116554 A2 | 3/2001 |
| WO | 0116554 A3 | 9/2001 |
| WO | 2005091014 A1 | 9/2005 |
| WO | 2008001092 A2 | 1/2008 |
| WO | 2012055148 A1 | 5/2012 |
| WO | 2017180985 A1 | 10/2017 |
| WO | 2018050913 A1 | 3/2018 |
| WO | 2018213757 A1 | 11/2018 |
| WO | 2018234394 A1 | 12/2018 |

OTHER PUBLICATIONS

Aumann, H.M. et al., "Doppler radar microphone with logarithmic square-law detector," Electronics Letters, vol. 52, No. 12, Jun. 2016, pp. 1061-1063.

Avargel, Y. et al., "Speech measurements using a laser Doppler vibrometer sensor: Application to speech enhancement," 2011 Joint Workshop on Hands-free Speech Communication and Microphone Arrays, May 30-Jun. 1, 2011, Edinburgh, UK, IEEE.

Chazal, P. et al., "Sleep/wake measurement using a noncontact biomotion sensor," Journal of Sleep Research, vol. 20, No. 2, Aug. 2010, pp. 356-366.

Chernov, N. et al., "Least Squares Fitting of Circles," Journal of Mathematical Imaging and Vision, vol. 23, No. 3, Nov. 2005, pp. 239-252.

Chung, K-Y. et al., "Noncontact Sleep Study by Multi-Modal Sensor Fusion," Sensors, vol. 17, No. 7, Jul. 2017, MDPI, 17 pages.

Davis, A. et al., "The Visual Microphone: Passive Recovery of Sound from Video," ACM Transactions on Graphics, vol. 33, No. 4, Jul. 2014, 10 pages.

Guan, S. et al., "Automated DC Offset Calibration Strategy for Structural Health Monitoring Based on Portable CW Radar Sensor," IEEE Transactions on Instrumentation and Measurement, vol. 63, No. 12, Dec. 2014, IEEE, pp. 3111-3118.

Geisheimer, J.L. et al., "A Surface Vibration Electromagnetic Speech Sensor," Multi-modal Speech Recognition Workshop 2002, Jun. 2002, Georgia Tech Research Institute, Atlanta Sensors and Electromagnetic Applications Lab, 5 pages.

Immoreev, I. et al., "UWB Radar for Patient Monitoring," IEEE Aerospace and Electronic Systems Magazine, vol. 23, Issue 11, Nov. 2008, IEEE, 8 pages.

Jiao, M. et al., "A Novel Radar Sensor for the Non-Contact Detection of Speech Signals," Sensors, vol. 10, No. 5, May 2010, pp. 4622-4633.

Lazaro, A. et al., "Analysis of Vital Signs Monitoring Using an IR-UWB Radar," Progress In Electromagnetics Research, vol. 100, Jan. 2010, pp. 265-284.

Lee, J.-M. et al., "Comparison of Wearable Trackers' Ability to Estimate Sleep," International Journal of Environmental Research and Public Health, vol. 15, No. 6, Jun. 2018, MDPI, 13 pages.

Li, C. et al., "Complex Signal Demodulation and Random Body Movement Cancellation Techniques for Non-contact Vital Sign Detection," 2008 IEEE MTT-S International Microwave Symposium Digest, Jun. 15-20, 2008, Atlanta, GA, USA, IEEE, 4 pages.

Mercuri, M. et al., "Vital-sign monitoring and spatial tracking of multiple people using a contactless radar-based sensor," Nature Electronics, vol. 2, Jun. 2019, pp. 252-262.

Nam, Y. et al., "Sleep Monitoring Based on a Tri-Axial Accelerometer and a Pressure Sensor," Sensors, vol. 16, No. 5, May 2016, MDPI, 14 pages.

Park, B.-K. et al., "Arctangent Demodulation With DC Offset Compensation in Quadrature Doppler Radar Receiver Systems," IEEE Transactions on Microwave Theory and Techniques, vol. 55, No. 5, May 2007, IEEE, pp. 1073-1079.

Rahmati, M. et al., "SSFB: Signal-Space-Frequency Beamforming for Underwater Acoustic Video Transmission," 2017 IEEE 14th International Conference on Mobile Ad Hoc and Sensor Systems (MASS), Oct. 22-25, 2017, Orlando, FL, USA, IEEE, pp. 180-188.

Ren, L. et al., "Noncontact Heartbeat Detection using UWB Impulse Doppler Radar," 2015 IEEE Topical Conference an Biomedical Wireless Technologies, Networks, and Sensing Systems (BioWireleSS), Jan. 25-28, 2015, San Diego, CA, IEEE, 3 pages.

Ren, L. et al., "Phase-Based Methods for Heart Rate Detection Using UWB Impulse Doppler Radar," IEEE Transactions on Microwave Theory and Techniques, vol. 64, Issue 10, Oct. 2016, IEEE, 13 pages.

Rong, Y. et al., "Harmonics-Based Multiple Heartbeat Detection at Equal Distance using UWB Impulse Radar," 2018 IEEE Radar Conference (RadarConf18), Apr. 23-27, 2018, Oklahoma City, OK, USA, IEEE, 5 pages.

Rong,Y. et al., "Remote Sensing for Vital Information Based on Spectral-Domain Harmonic Signatures," IEEE Transactions on Aerospace and Electronic Systems, vol. 55, No. 6, May 2019, IEEE, 12 pages.

Rong, Y. "Remote Sensing For Vital Signs Monitoring Using Advanced Radar Signal Processing Techniques," A Dissertation Presented in Partial Fulfillment of the Requirements for the Degree Doctor of Philosophy, Arizona State University, Dec. 2018, 117 pages.

Rong, Y. et al., "Smart Homes: See Multiple Heartbeats Through Wall Using Wireless Signals," 2019 Radar Conference (RadarConf), Apr. 2019, Boston, MA, USA, IEEE, 6 pages.

Rothberg, S. et al., "Laser vibrometry: Pseudo-vibrations," Journal of Sound and Vibration, Dec. 1989, Elsevier, 18 pages.

(56) References Cited

OTHER PUBLICATIONS

Savage, H.O. et al., "Development and validation of a novel non-contact monitor of nocturnal respiration for identifying sleep-disordered breathing in patients with heart failure," ESC Heart Failure, vol. 3, No. 3, Sep. 2016, John Wiley & Sons, pp. 212-219.
Staderini, E.M., "UWB Radars in Medicine," IEEE Aerospace and Electronic Systems Magazine, vol. 17, No. 1, Feb. 2002, pp. 13-18.
Tian, Y. et al., "Smart radar sensor for speech detection and enhancement," Sensors and Actuators A: Physical, vol. 191, Mar. 2013, Elsevier, pp. 99-104.
Viswanathan, V. et al., "Noise-immune multisensor speech input: formal subjective testing in operational conditions," International Conference on Acoustics, Speech, and Signal Processing, May 23-26, 1989, Glasgow, UK, IEEE, pp. 373-376.
Viswanathan, V. et al., "Noise-immune speech transduction using multiple sensors," IEEE International Conference on Acoustics, Speech, and Signal Processing (ICASSP'85), Apr. 26-29, 1985, Tampa, FL, USA, IEEE, 4 pages.
Yacchirema, D.C., "A Smart System for Sleep Monitoring by Integrating IoT With Big Data Analytics," IEEE Access, vol. 6, Jun. 2018, 16 pages.
Zhao, H. et al., "A Portable 24-GHz Auditory Radar for Non-contact Speech Sensing with Background Noise Rejection and Directional Discrimination," 2016 IEEE MTT-S International Microwave Symposium (IMS), May 22-27, 2016, San Francisco, CA, USA, IEEE, 4 pages.
Invitation to Pay Additional Fees for International Patent Application No. PCT/US2019/053425, dated Nov. 27, 2019, 2 pages.
International Search Report and Written Opinion for International Patent Application No. PCT/US2019/053425, dated Jan. 30, 2020, 10 pages.
International Preliminary Report on Patentability for International Patent Application No. PCT/US2019/053425, dated Apr. 15, 2021, 7 pages.
International Search Report and Written Opinion for International Patent Application No. PCT/US2020/057452, dated Feb. 12, 2021, 11 pages.
International Search Report and Written Opinion for International Patent Application No. PCT/US2020/058326, dated Feb. 3, 2021, 13 pages.
Author Unknown, "XeThru X4," available as early as Apr. 40, 2019, accessed Jun. 9, 2022 from https://www.radartutorial.eu/19.kartei/13.labs/karte009.en.html, 1 page.
Lee, J. et al., "Sleep Monitoring System Using Kinect Sensor," International Journal of Distributed Sensor Networks, vol. 11, No. 10, Oct. 2015, Hindawi Publishing Corporation, 10 pages.
Ma, Y. et al., "Speech Recovery Based On Auditory Radar and Webcam," 2019 IEEE MTT-S International Microwave Biomedical Conference (IMBioC), May 6-8, 2019, Nanjing, China, IEEE, 3 pages.
Extended European Search Report for European Patent Application No. 20882810.3, dated Nov. 22, 2022, 9 pages.
Non-Final Office Action for U.S. Appl. No. 17/773,503, dated Mar. 14, 2023, 23 pages.

\* cited by examiner

METHODS AND SYSTEMS FOR REMOTE SLEEP MONITORING

RELATED APPLICATIONS

This application is a 35 USC 371 national phase filing of International Application No. PCT/US2020/057452, filed Oct. 27, 2020, which claims the benefit of U.S. Provisional Patent Application No. 62/926,717, filed Oct. 28, 2019, the disclosures of which are incorporated herein by reference in their entireties.

FIELD OF THE DISCLOSURE

The present disclosure relates to vital sign estimation and monitoring.

BACKGROUND

Sleep monitoring tracks the activity of the human body during sleep and provides information on brain activity and other physiological factors during sleep. Hence, sleep monitoring has been used to diagnose or understand the underlying causes of sleeping disorders such as sleep apnea, sleep related seizures, insomnia, etc., and also to qualitatively measure different aspects of sleep such as quality, activity, etc.

Common methods of sleep monitoring require the use of wearables or other contact sensors to measure vital signs. Such wearables can be uncomfortable to wear and can cause difficulty in falling asleep or even affect sleep behavior itself. Furthermore, several of these approaches also require overnight monitoring in clinics, increasing cost and discomfort of patients. For these reasons, non-contact approaches for sleep monitoring have tremendous utility.

Research into sleep monitoring approaches has been varied. As mentioned above, sleep monitoring using wearables is one of the most common approaches. Non-contact sleep monitoring approaches also exist, such as camera-based and sensor-based approaches. One example uses a low power radar-based biomotion sensor that detects movement to measure sleep/wake patterns during sleep and perform sleep/wake classification.

SUMMARY

Methods and systems for remote sleep monitoring are provided. Such methods and systems provide non-contact sleep monitoring via remote sensing or radar sensors. In this regard, when processing backscattered radar signals from a sleeping subject on a normal mattress, a breathing motion magnification effect is observed from mattress surface displacement due to human respiratory activity. This undesirable motion artifact causes existing approaches for accurate heart-rate estimation to fail. Embodiments of the present disclosure use a novel active motion suppression technique to deal with this problem by intelligently selecting a slow-time series from multiple ranges and examining a corresponding phase difference. This approach facilitates improved sleep monitoring, where one or more subjects can be remotely monitored during an evaluation period (which corresponds to an expected sleep cycle).

An exemplary embodiment provides a method for remote sleep monitoring. The method includes transmitting a radar signal toward a subject and receiving a radio frequency (RF) response signal corresponding to the radar signal. The method further includes monitoring vital signs of a subject, which includes processing the RF response signal to produce one or more vital sign signals and monitoring the vital sign signals over an evaluation period. The method further includes classifying a sleep state of the subject based on results from monitoring the vital signs.

Another exemplary embodiment provides a sleep monitoring device. The sleep monitoring device includes a radar sensor configured to receive an RF response signal to a radar signal and a processing circuit coupled to the radar sensor. The processing circuit is configured to monitor vital signs of a subject from the RF response signal by processing the RF response signal to produce a plurality of vital sign signals and classifying a sleep state of the subject based on monitoring the plurality of vital sign signals over an evaluation period.

Another exemplary embodiment provides a system for remote sleep monitoring. The system includes a radar sensor configured to receive an RF response signal to a radar signal transmitted toward one or more subjects, a database, and a processing circuit coupled to the radar sensor and the database. The processing circuit is configured to monitor vital signs of the one or more subjects over an evaluation period by processing the RF response signal to produce vital sign signals for each of the one or more subjects, storing the vital sign signals in the database, and classifying a sleep state of the subject based on the vital sign signals stored in the database.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1A:
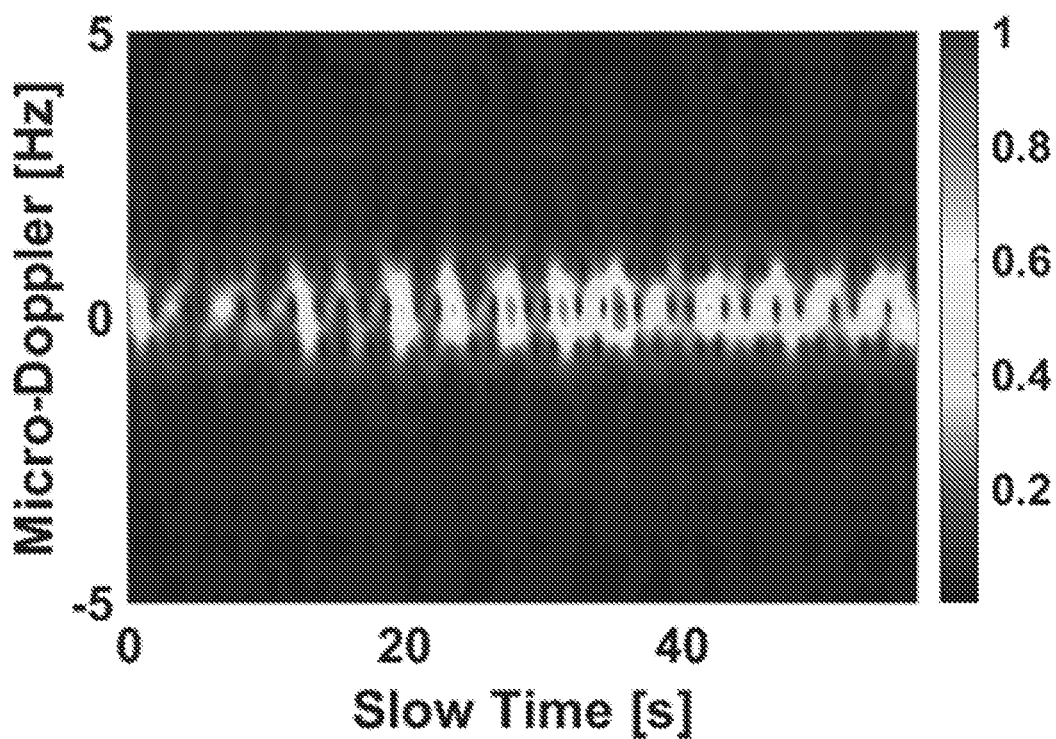
FIG. 1A is a graphical representation of a vital sign micro-Doppler signature in slow time for a subject lying on a rigid surface.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Methods and systems for remote sleep monitoring are provided. Such methods and systems provide non-contact sleep monitoring via remote sensing or radar sensors. In this regard, when processing backscattered radar signals from a sleeping subject on a normal mattress, a breathing motion magnification effect is observed from mattress surface displacement due to human respiratory activity. This undesirable motion artifact causes existing approaches for accurate heart-rate estimation to fail. Embodiments of the present disclosure use a novel active motion suppression technique to deal with this problem by intelligently selecting a slow-time series from multiple ranges and examining a corresponding phase difference. This approach facilitates improved sleep monitoring, where one or more subjects can be remotely monitored during an evaluation period (which corresponds to an expected sleep cycle).

I. Signal Model

Remote vital sign detection (e.g., for remote sleep monitoring) can be characterized with a signal model. For example, a synthesized transmitted pulse for remote vital sign detection can be modeled as a cosine wave with a Gaussian envelope:

$$p_{tx}(\tau) = p_0(\tau)\cos(2\pi F_c \tau) \quad \text{Equation 1}$$

where $p_0(\tau)$ denotes the Gaussian pulse envelope and is designed to satisfy an emission mask. $F_c$ denotes the nominal operating frequency. A receive signal in response to the transmitted pulse can be modeled as:

$$p_{rx}(\tau) = A_T p_0(\tau - \tau_D(t))\cos(2\pi F_c(\tau - \tau_D(t))) \quad \text{Equation 2}$$

where $A_T$ denotes the target response and $T_D(t)$ denotes time-varying time-delay due to vital sign motion. T and t denote slow-time and fast-time scales, respectively.

The vital sign motion V(t) of a subject at a nominal distance $d_0$ can be modeled as a sum of two non-stationary and periodic-like signals, $X_B(t)$ for respiratory activity and $X_H(t)$ for cardiac activity:

$$d(t) = d_0 + V(t) = d_0 + X_B(t) + X_H(t) \quad \text{Equation 3}$$

Then the motion modulated time-delay is written as $T_D(t) = d(t)/c$, where c is the speed of light.

The complex baseband signal is obtained by mixing with a term $e^{j2\pi F_c \tau}$ and low pass filtering:

$$s(t) = A(t)e^{j2\pi F_c \tau_D(t)} \quad \text{Equation 4}$$

where A(t) denotes a time-varying amplitude. The ideal phase signal is then derived as:

$$\phi(t) = \frac{4\pi X_B(t)}{\lambda} + \frac{4\pi X_H(t)}{\lambda} + \varphi_0 \quad \text{Equation 5}$$

where $\lambda = c/F_c$ represents wavelength and $\varphi_0$ is the initial phase term.

II. Breathing Magnification Effect

An interesting motion artifact has been observed during a sleep monitoring study. This motion magnification effect on the respiration signal makes heartbeat detection impossible using existing methods, such as radar-based methods.

In general, the respiration signal in the radar return is much stronger than that of heartbeat signal for two factors: radar cross section and physical displacement. Even though a radar sensor is illuminating the entire body of a subject, only a small portion of this response contains skin motion or vasomotion due to cardiac activity. The physical displacement due to normal breathing ranges from 1 mm (shallow) to 1 cm (deep), while the physical displacement near the skin surface as a result of heartbeat motion is on the order of 0.1 mm. Furthermore, in supine position, a non-rigid mattress tends to support and conform to the back of the human body very well. This results in the mattress moving with the human body during respiration, causing a motion magnification effect due to respiration.

Figure 1B:
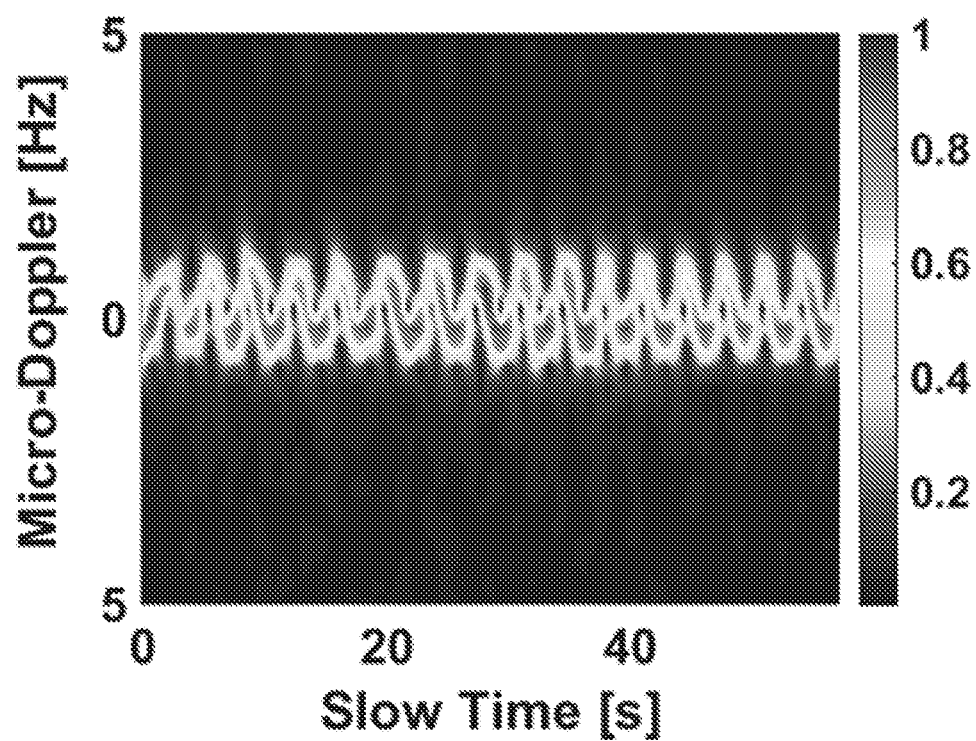
FIG. 1B is a graphical representation of a vital sign micro-Doppler signature in slow time for a subject lying on a non-rigid surface.

FIGS. 1A and 1B demonstrate the motion magnification effect due to mattress surface displacement during respiration. FIG. 1A is a graphical representation of a vital sign micro-Doppler signature in slow time for a subject lying on a rigid surface. FIG. 1B is a graphical representation of a vital sign micro-Doppler signature in slow time for a subject lying on a non-rigid surface.

In order to validate this important observation, a test subject was instructed to lie down on both a rigid firm surface (e.g., a wooden bed frame) and on a non-rigid surface (e.g., a soft mattress) and breathe normally. Radar response signals for both situations were recorded and processed for comparison. As illustrated in FIGS. 1A and 1B, the non-rigid surface resulted in a relatively large magnification of breathing motion artifacts.

III. Active Motion Suppression Technique

Prior work has shown that radar-based heartbeat detection is respiration-interference limited. In supine position on a non-rigid surface, this problem gets even more challenging, as explained above with respect to FIGS. 1A and 1B. As a result, the spectral representation of the slow-time series at the range bin of interest, which contains significant motion energy, only shows respiration spectral energy with elevated sidelobes around the main lobe as well as an increased noise-floor. The weak heartbeat spectral feature is overwhelmed by the enhanced respiration signal.

Embodiments described herein provide a new active motion suppression technique to recover the heartbeat signal in the presence of magnified respiration interference. This approach exploits the fact that the human body is an extended dynamic target, and thus vital signs can be observed in multiple range bins. Across these multiple range bins, breathing energy spreads across a larger number of range bins when compared to heartbeat or pulse energy. The total number of range bins of interest can be divided into two categories: breathing only, and a mixture of respiration and heartbeat signals. A goal of the active motion suppression technique is to find two 'best' range bins such that their phase difference in the slow-time series generates a maximum pulse signal to noise ratio (SNR).

Figure 2:
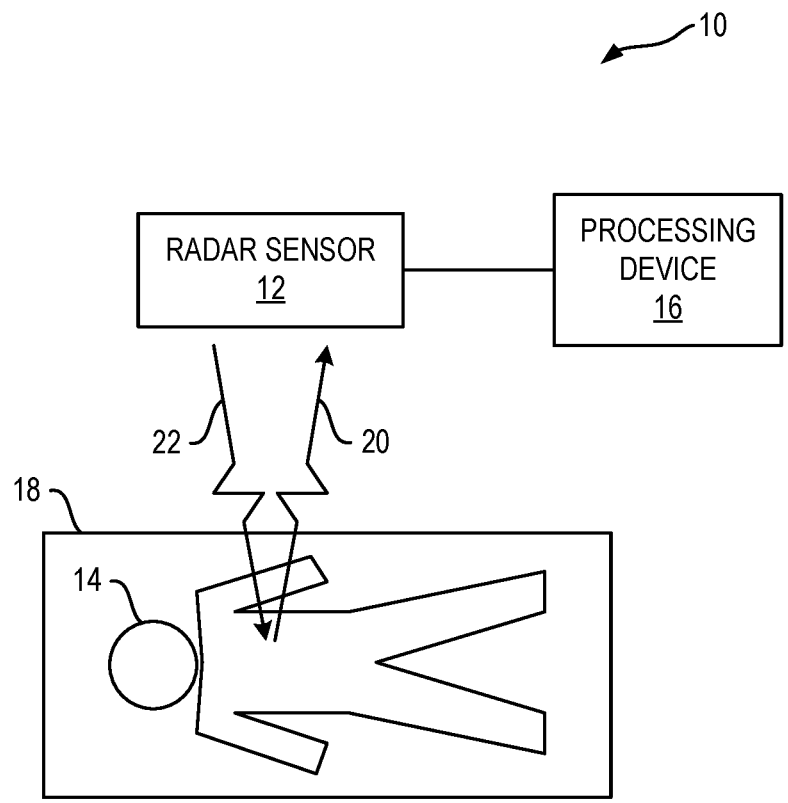
FIG. 2 is a schematic diagram of an exemplary system for remote sleep monitoring.

FIG. 2 is a schematic diagram of an exemplary system 10 for remote sleep monitoring. The system includes a radar sensor 12 positioned at a distance from a subject 14. The radar sensor 12 is in communication with a processing device 16, such as a computer system.

In an exemplary aspect, the subject 14 lies on a rigid or non-rigid surface 18 (e.g., a mattress and/or a rigid frame) during a sleep evaluation (e.g., an evaluation period corresponding to an expected sleep cycle, such as four or more hours, six or more hours, or eight or more hours). The radar sensor 12 is configured to receive (e.g., sense) a radio frequency (RF) response signal 20 which corresponds to a radar signal 22 emitted toward the subject 14. In some examples, the radar sensor 12 is a transceiver which transmits the radar signal 22 and receives the RF response signal 20. In other examples, the radar signal 22 is emitted from another device (e.g., a transmitter which may be in communication with the radar sensor 12). The processing device 16 records and/or analyzes the RF response signal 20 to produce and/or monitor vital signs of the subject. The processing device 16 is further used to classify a sleep state of the subject (e.g., awake, asleep, depth of sleep, etc.), and may also provide a diagnosis of sleep conditions (e.g., sleep apnea, insomnia, etc.).

Figure 3:
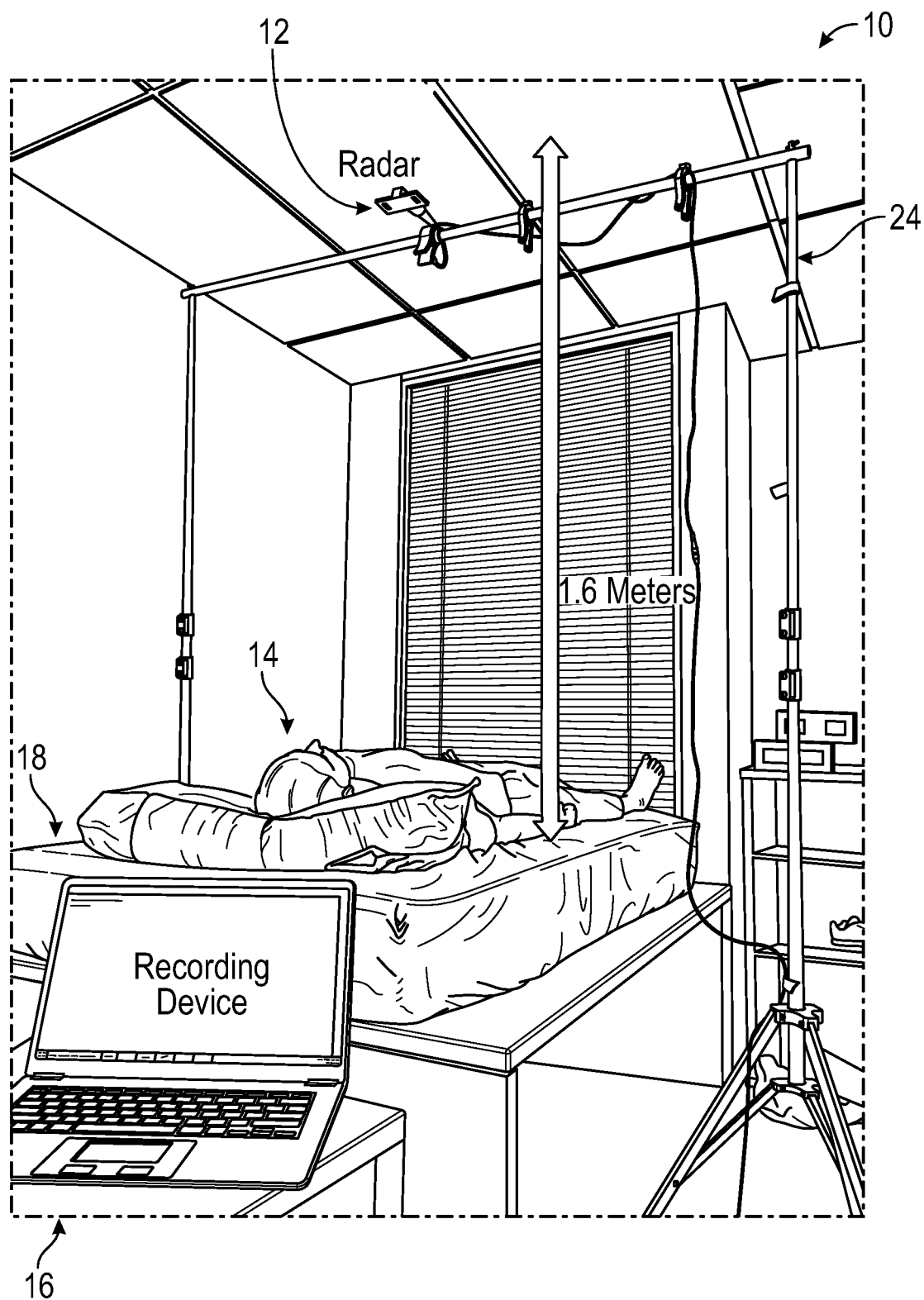
FIG. 3 is an image of an embodiment of the system for remote sleep monitoring of FIG. 2.

FIG. 3 is an image of an embodiment of the system 10 for remote sleep monitoring of FIG. 2. In this embodiment, the subject 14 lies on a non-rigid surface 18 (e.g., a mattress) which is on an elevated platform. The radar sensor 12 is suspended above the subject 14 via a ceiling mount or frame 24 and is pointed at the torso of the subject 14. For evaluation purposes, a test subject 14 was also fitted with a photoplethysmogram (PPG) sensor, which was used as a reference signal in a sleep monitor study. However, embodiments may omit such contact sensors.

The radar sensor 12 in the embodiment of FIG. 3 includes an impulse-based ultra-wide band (UWB) radar. In some examples, the UWB radar operates at 1.4 gigahertz (GHz) in the X band with low power emission, satisfying FCC part 15. A coherent transceiver is achieved through precise timing control. For slow motion monitoring (e.g., vital signs), many pulses can be coherently combined to achieve sufficient processing gain. The theoretical range resolution is about 10 cm. In a higher SNR regime, the actual range resolution is much smaller and on the order of 1 cm. In order to maximize the SNR of the response signal, the radar system parameters may be configured to operate at the highest possible pulse integration level while meeting the minimum range requirement for vital sign monitoring. Fine ranging information from the UWB radar provides multiple spatially independent observations at the same time. Thus, embodiments may effectively turn heartbeat detection into a multi-channel source separation problem.

It should be understood that in other embodiments the radar sensor 12 can include a different radar, such as a having a bandwidth between 1.0 GHz and 2.0 GHz. It should also be understood that the radar sensor 12 may in other embodiments be positioned differently, such as wall-mounted or as a free-standing device placed on a surface and aimed toward the subject 14.

Figure 4:
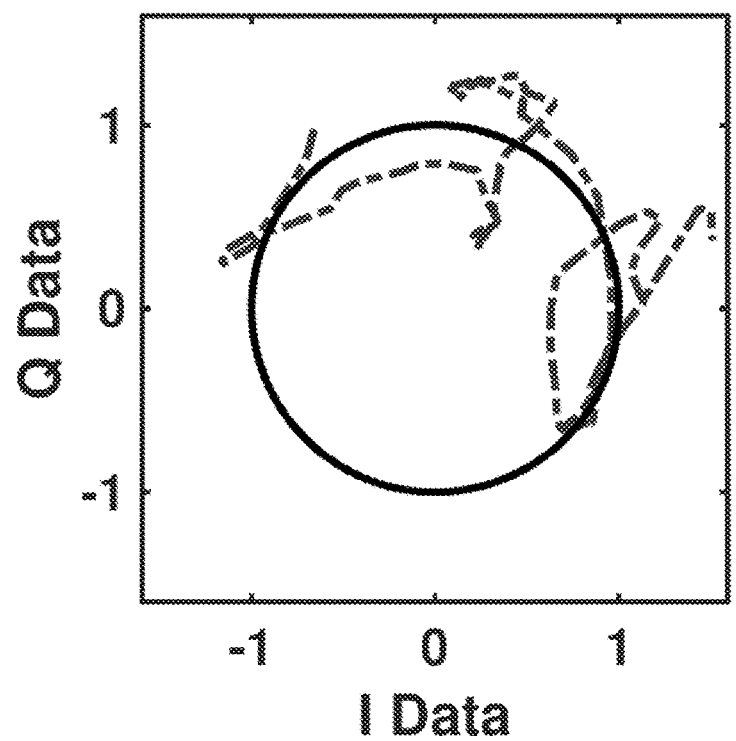
FIG. 4 is an in-phase/quadrature (I/Q) data constellation plot from an example noisy channel due to excessive phase noise.
Figure 5:
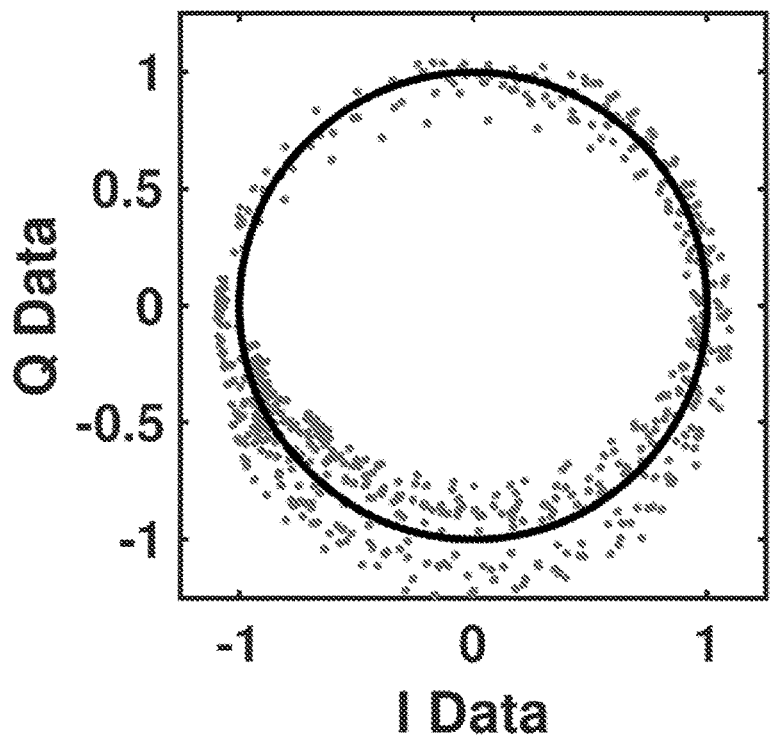
FIG. 5 is an I/Q data constellation plot of an example range bin used to actively suppress breathing motion.

With reference to FIGS. 4 and 5, range bin selection for the active motion suppression technique is described. In an exemplary aspect, the initial group of range bins is selected by range gating spatio-temporal data (e.g., such as represented by a spatio-temporal heat map). To obtain a correct phase variation, which is linearly related to motion, complex signals from each candidate bin (e.g., spatial channel) are further processed by applying a circle fitting algorithm. The purpose of curve fitting is to correct for direct current (DC) offset, $\mathcal{D}$, as shown in Equation 6:

$$\Phi(t) = \text{unwrapping} \{A \tan(Q(t)/I(t))\} \quad \text{Equation 6}$$

$$= \text{unwrapping} \left\{ A \tan \left[ \frac{A_0 \sin\left(\frac{4\pi V(t)}{\lambda} + \varphi_0\right) + \mathcal{D}_Q}{A_0 \cos\left(\frac{4\pi V(t)}{\lambda} + \varphi_0\right) + \mathcal{D}_I} \right] \right\}$$

$$= \text{unwrapping} \left\{ A \tan \left[ \frac{A_0 \sin\left(\frac{4\pi V(t)}{\lambda} + \varphi_0\right)}{A_0 \cos\left(\frac{4\pi V(t)}{\lambda} + \varphi_0\right)} \right] \right\}$$

$$= \frac{4\pi V(t)}{\lambda} + \varphi_0$$

where $A_0$ is a nominal signal amplitude.

FIG. 4 is an in-phase/quadrature (I/Q) data constellation plot from an example noisy channel due to excessive phase noise. Clean phase samples should be mostly located closely to the unit circle in the I/Q constellation plot. One empirical criterion to evaluate the quality of phase information in each channel is to check the root mean square error (RMSE) of the distance between the sample points and the unit circle:

$$d_{err} = \sqrt{\Sigma(\sqrt{I^2+Q^2}-1)^2/N} \leq 0.3 \quad \text{Equation 7}$$

Here the upper limit is selected as thirty percent of the unit radius, which means that if the distance error from the I/Q samples is over 0.3, then this channel is too noisy and thus is ignored.

By now, a set of channels or range bins, V, with clean phase is obtained with outliers eliminated. But each set of I/Q samples from the selected range bins can generate a different phase trajectory with varying arc lengths and starting phases in the constellation plot. An example is shown in FIG. 4 to demonstrate the results. The example demonstrates the magnified phase response because of the motion magnification effect described above in Section II. Based on the radar parameters, the expected phase rotation is about 90 degrees assuming the motion amplitude of breathing is 5 mm. This observation implies that one or a small set of range bins in V can be selected for heartbeat detection based on the expected phase rotation $arc_0$. Mathematically, this process of choosing range bins, V, that most likely have clean vital sign signals is expressed as $\{V|d'_j s;$ such that $arc_i \leq arc_0\}$.

FIG. 5 is an I/Q data constellation plot of an example range bin used to actively suppress breathing motion. It is observed that the above method works very well. However, some embodiments focus on adaptive motion suppression, in which range bins with phase $arc \leq arc_0$ and range bins with phase $arc > arc_0$ (as seen in FIG. 4) are used to actively suppress breathing motion. Note that different range bins i' will have different phase offsets $\phi_{i'}$ as the static phase is linearly related to the distance.

The basic idea of phase-based motion cancellation to suppress the magnified respiration signal is to select one channel from the breathing only range bins and select another one from the range bins containing both respiration and heartbeat signals:

$$\Phi_{m,B}(t) = \frac{4\pi X_B(t)}{\lambda} + \varphi_{m,0} \quad \text{Equation 8}$$

$$\Phi_{n,V}(t) = \frac{4\pi (X_B(t) + X_H(t))}{\lambda} + \varphi_{n,0} \quad \text{Equation 9}$$

where the DC offsets in the m-th channel and the n-th channel are assumed to be compensated perfectly. Ideally, the phase difference is only a function of the heartbeat signal:

$$\Phi_{Diff}(t) = \Phi_{n,V}(t) - \Phi_{m,B}(t) \quad \text{Equation 10}$$
$$= \frac{4\pi X_H(t)}{\lambda} + \varphi_{n,0} - \varphi_{m,0}$$

But in reality the motion interference cannot be perfectly cancelled out due to phase noise. This leads to an extra term in Equation 10, representing motion residual noise $X_B^{Resi}(t)$:

$$\tilde{\Phi}_{Diff}(t) = \frac{4\pi (X_B^{Resi}(t) + X_H(t))}{\lambda} + \varphi_{n,0} - \varphi_{m,0} \quad \text{Equation 11}$$

where $\|X_B^{Resi}(t)\|_2 \ll \|X_B(t)\|_2$

The two most appropriate channels are chosen based on the following equation:

$$\arg\max_{m,n} \mathcal{SNR}_H \quad \text{Equation 12}$$

The phase difference of any combination from the set of channels V (obtained as described above with respect to FIG. 4) produces the best pulse SNR, $\mathcal{SNR}_H$, and this combination gets selected. $\mathcal{SNR}_H$ is defined as the signal to noise ratio at the heartbeat frequency of interest by inspecting the spectrum of the phase differences $\tilde{\Phi}_{Diff}(t)$.

Figure 6:
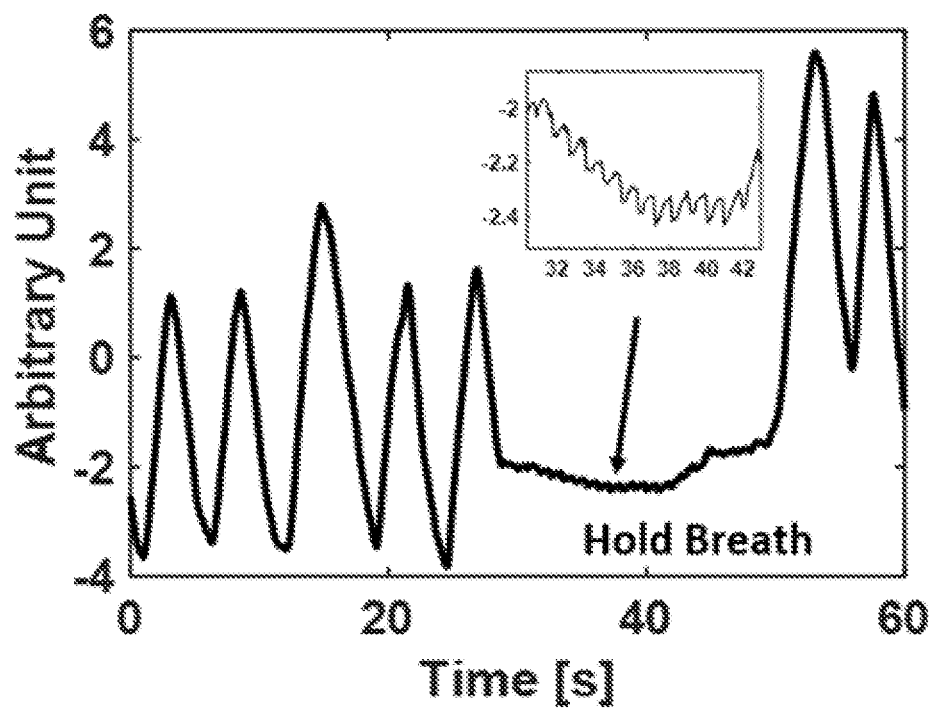
FIG. 6 is a graphical representation of a temporal wave containing both respiration and heartbeat signals while a subject is piece-wise breathing.
Figure 7:
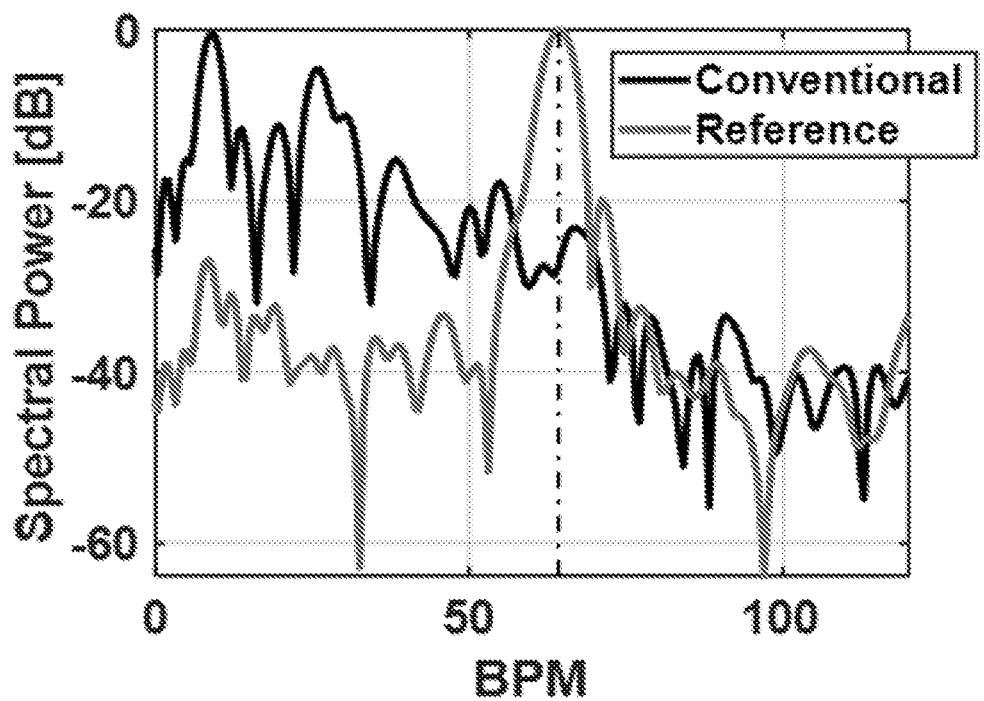
FIG. 7 is a graphical representation of a vital sign spectrum obtained with a conventional approach and a reference heartbeat signal spectrum.
Figure 8:
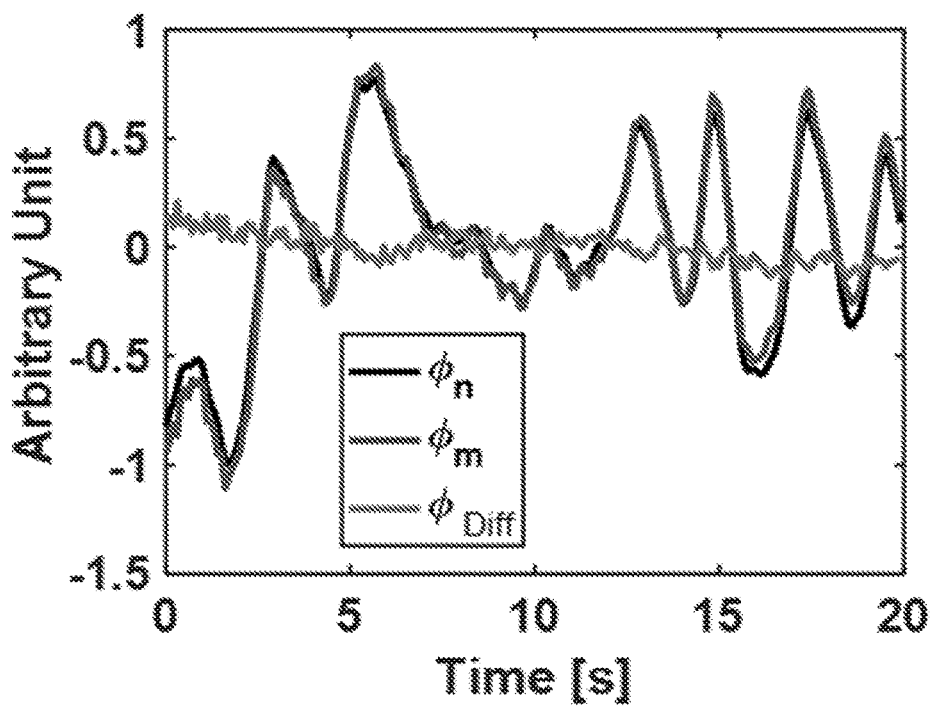
FIG. 8 is a graphical representation of phase variations from two range bins along with the phase difference of the two range bins.
Figure 9:
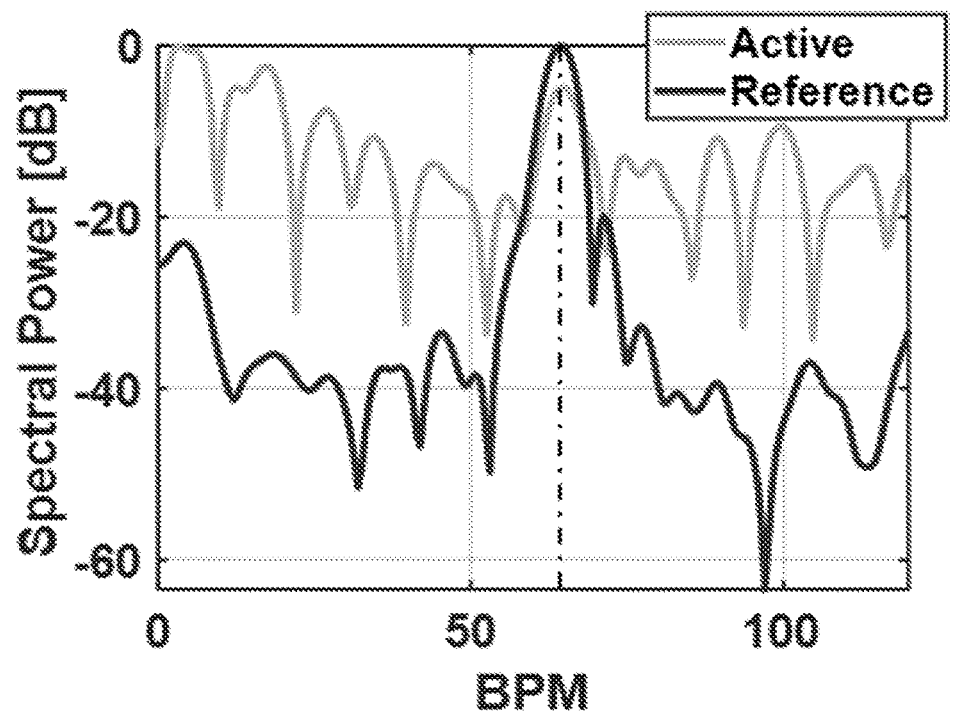
FIG. 9 is a graphical representation of a vital sign spectrum obtained with active motion suppression and a reference heartbeat signal spectrum.

With reference to FIGS. 6-8, exemplary results of applying the active motion suppression technique are described. These results were obtained using the system for remote sleep monitoring of FIGS. 2 and 3. A first example, described below with respect to FIG. 6, shows results when a subject is holding a breath (e.g., breathing piece-wise). When the subject is holding a breath, the breathing motion and associated breathing artifacts are not present anymore. A second example, described below with respect to FIGS. 7-9, compares results from a conventional approach against embodiments of the active motion suppression technique.

FIG. 6 is a graphical representation of a temporal wave containing both respiration and heartbeat signals while a subject is piece-wise breathing. This illustrates a snapshot of the temporal wave containing both respiration and heartbeat signals at the range bin which has the strongest motion energy while the subject is piece-wise breathing. When the test subject stops breathing, the heartbeat pulse is clearly visible. There is no motion artifact present when breathing stops.

FIG. 7 is a graphical representation of a vital sign spectrum obtained with a conventional approach and a reference heartbeat signal spectrum. The range bin containing the maximum motion energy is used in FIG. 7. Only the possible breathing spectrum and its strong harmonic spectral features can be seen, along with an elevated noise floor. However, embodiments using the proposed active motion suppression technique can significantly improve the heartbeat detectability.

FIG. 8 is a graphical representation of phase variations from two range bins along with the phase difference of the two range bins. This figure compares phase variations from the two range bins in Equation 12, as well as their phase difference. It can be seen that the overall trend of breathing patterns is almost removed, and thus the phase residual has an almost constant, pulse-like shape.

FIG. 9 is a graphical representation of a vital sign spectrum obtained with active motion suppression and a reference heartbeat signal spectrum. By inspecting the vital sign spectrum of the phase difference in FIG. 8, the respiration signal is significantly suppressed, and the heartbeat is correctly recovered as the detected heartbeat has the same BPM as the reference pulse signal.

In order to demonstrate the effectiveness of motion suppression through the proposed technique, no filter is applied in generating FIG. 9. Additionally, the two phases in Equation 10 are normalized to a similar scale before taking the difference. In other embodiments, additional filtering is applied to the reference heartbeat signal spectrum to further improve results.

IV. Method for Remote Sleep Monitoring

Figure 10:
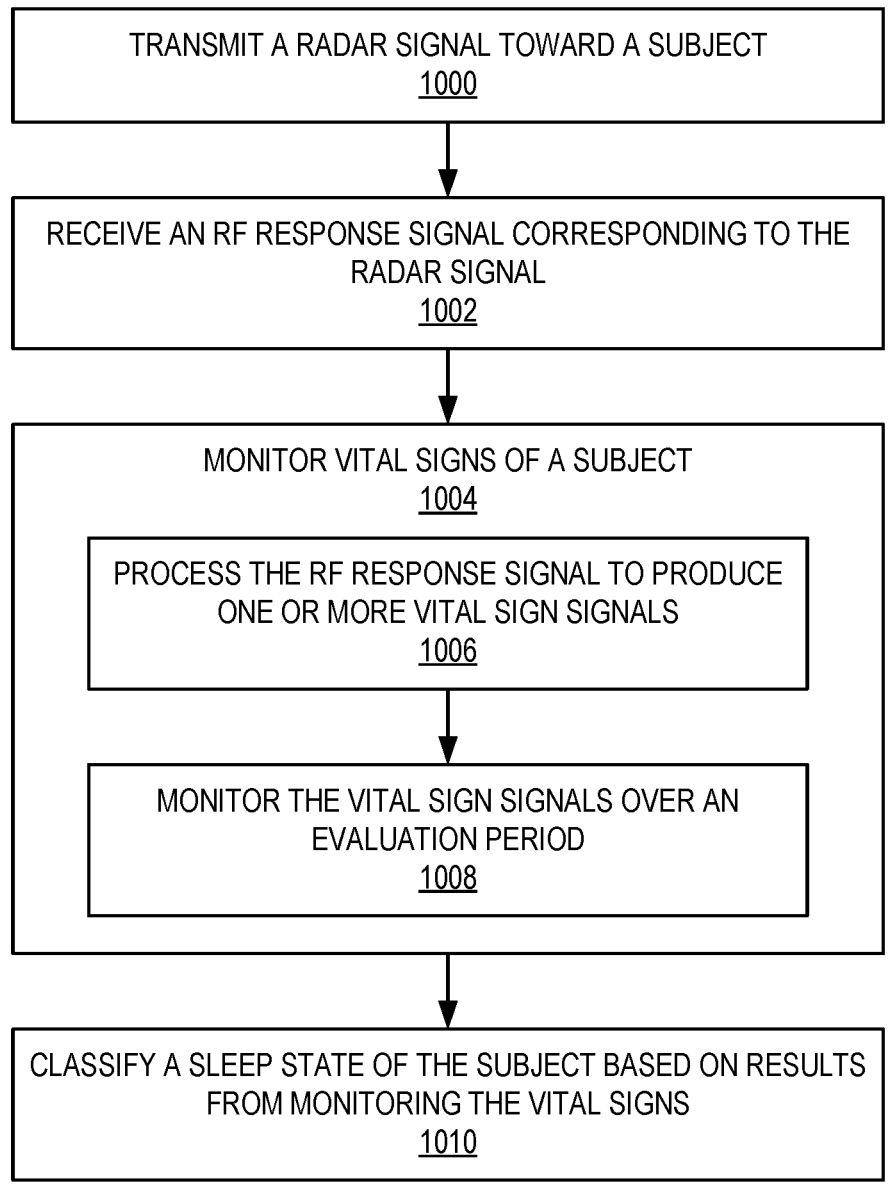
FIG. 10 is a flow diagram illustrating a process for remote sleep monitoring.

FIG. 10 is a flow diagram illustrating a process for remote sleep monitoring. The process begins at operation 1000, with transmitting a radar signal toward a subject. The process continues at operation 1002, with receiving an RF response signal corresponding to the radar signal. In an exemplary aspect, the radar sensor 12 of FIGS. 2 and 3 sends a series of UWB radar impulses and receives the RF response signal. The RF response signal may include one or more vital sign micro-Doppler spatial signatures (e.g., respiratory and cardiac signatures), at least some of which may be enhanced by displacement of a mattress or other non-rigid surface in contact with the subject.

The process continues at operation 1004, with monitoring vital signs of a subject. Operation 1004 includes suboperation 1006, with processing the RF response signal to produce one or more vital sign signals. In an exemplary aspect, processing the RF response signal includes processing the RF response signal to produce a respiratory signal (e.g., from a respiratory channel) and a mixed respiratory and cardiac spatial channel and extracting a cardiac signal from the mixed respiratory and cardiac spatial channel. Operation 1004 further includes suboperation 1008, with monitoring the vital sign signals over an evaluation period. In an exemplary aspect, the evaluation period corresponds to an expected sleep cycle of the subject.

The process continues at operation 1010, with classifying a sleep state of the subject based on results from monitoring the vital signs. For example, the sleep state of the subject (e.g., awake, asleep, depth of sleep, etc.) may be determined throughout the evaluation period (e.g., to determine duration and/or quality of sleep). This analysis of the vital sign signals, including classification of the sleep state may also be used to provide a diagnosis of sleep conditions (e.g., sleep apnea, insomnia, etc).

Although the operations of FIG. 10 are illustrated in a series, this is for illustrative purposes and the operations are not necessarily order dependent. Some operations may be performed in a different order than that presented. Further, processes within the scope of this disclosure may include fewer or more steps than those illustrated in FIG. 10.

V. Computer System

Figure 11:
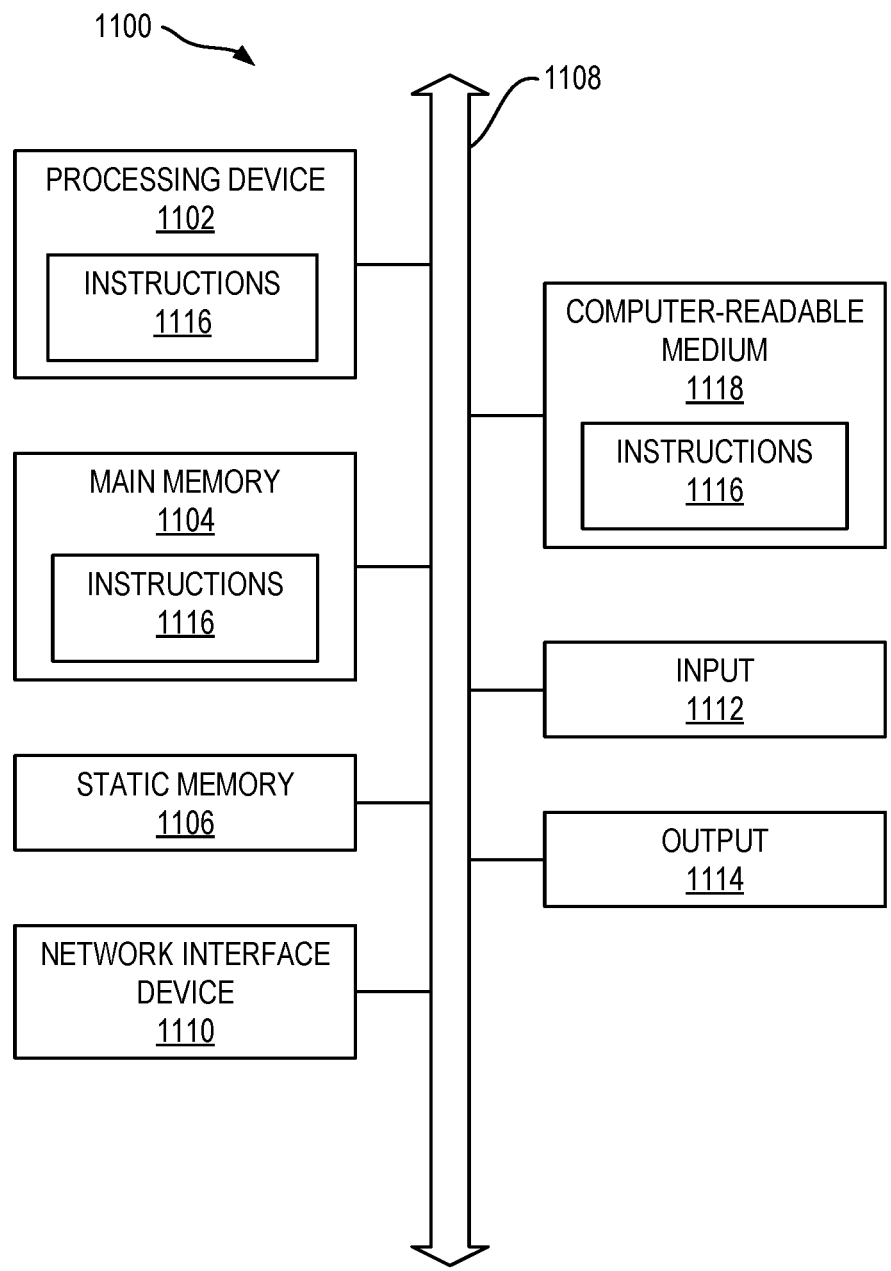
FIG. 11 is a schematic diagram of a generalized representation of an exemplary computer system that could be used to perform any of the methods or functions described above, such as remote sleep monitoring.

FIG. 11 is a schematic diagram of a generalized representation of an exemplary computer system 1100 that could be used to perform any of the methods or functions described above, such as remote sleep monitoring. In some examples, the radar sensor 12 and/or the processing device 16 of FIGS. 2 and 3 are implemented as the computer system 1100. In this regard, the computer system 1100 may be a circuit or circuits included in an electronic board card, such as, a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The exemplary computer system 1100 in this embodiment includes a processing device 1102 or processor, a main memory 1104 (e.g., read-only memory (ROM), flash memory, dynamic random access memory (DRAM), such as synchronous DRAM (SDRAM), etc.), and a static memory 1106 (e.g., flash memory, static random access memory (SRAM), etc.), which may communicate with each other via a data bus 1108. Alternatively, the processing device 1102 may be connected to the main memory 1104 and/or static memory 1106 directly or via some other connectivity means. In an exemplary aspect, the processing device 1102 could be used to perform any of the methods or functions described above.

The processing device 1102 represents one or more general-purpose processing devices, such as a microprocessor, central processing unit (CPU), or the like. More particularly, the processing device 1102 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 1102 is configured to execute processing logic in instructions for performing the operations and steps discussed herein.

The various illustrative logical blocks, modules, and circuits described in connection with the embodiments disclosed herein may be implemented or performed with the processing device 1102, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 1102 may be a microprocessor, or may be any conventional processor, controller, microcontroller, or state machine. The processing device 1102 may also be implemented as a combination of computing devices (e.g., a combination of a DSP and a microprocessor, a plurality of microprocessors, one or more microprocessors in conjunction with a DSP core, or any other such configuration).

The computer system 1100 may further include a network interface device 1110. The computer system 1100 also may or may not include an input 1112, configured to receive input and selections to be communicated to the computer system 1100 when executing instructions. The input 1112 may include, but not be limited to, a touch sensor (e.g., a touch display), an alphanumeric input device (e.g., a keyboard), and/or a cursor control device (e.g., a mouse). In an exemplary aspect, the radar sensor 12 of FIGS. 2 and 3 is an input 1112 to the computer system 1100. The computer system 1100 also may or may not include an output 1114, including but not limited to a display, a video display unit (e.g., a liquid crystal display (LCD) or a cathode ray tube (CRT)), or a printer. In some examples, some or all inputs 1112 and outputs 1114 may be combination input/output devices. In an exemplary aspect, the radar sensor 12 of FIGS. 2 and 3 is also an output 1114 of the computer system 1100.

The computer system 1100 may or may not include a data storage device that includes instructions 1116 stored in a computer-readable medium 1118. The instructions 1116 may also reside, completely or at least partially, within the main memory 1104 and/or within the processing device 1102 during execution thereof by the computer system 1100, the main memory 1104, and the processing device 1102 also constituting computer-readable medium. The instructions 1116 may further be transmitted or received via the network interface device 1110.

While the computer-readable medium 1118 is shown in an exemplary embodiment to be a single medium, the term "computer-readable medium" should be taken to include a single medium or multiple media (e.g., a centralized or distributed database, and/or associated caches and servers) that store the one or more sets of instructions 1116. The term "computer-readable medium" shall also be taken to include any medium that is capable of storing, encoding, or carrying a set of instructions for execution by the processing device 1102 and that causes the processing device 1102 to perform any one or more of the methodologies of the embodiments disclosed herein. The term "computer-readable medium" shall accordingly be taken to include, but not be limited to, solid-state memories, optical medium, and magnetic medium.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. A method for remote sleep monitoring, the method comprising:
   transmitting a radar signal toward a subject;
   receiving a radio frequency (RF) response signal corresponding to the radar signal;
   monitoring vital signs of a subject, the vital signs comprising a respiratory signal and a cardiac signal, the monitoring of the vital signs comprising:
      processing the RF response signal, the processing comprising:
         producing vital sign signals, the vital sign signals comprising the respiratory signal and a mixed respiratory and cardiac spatial channel;
         extracting the cardiac signal from the mixed respiratory and cardiac spatial channel;
         producing spatio-temporal data of motion response in the RF response signal; and
         range gating the spatio-temporal data to produce a plurality of spatial channels comprising one or more respiratory spatial channels and one or more mixed respiratory and cardiac spatial channels; and
      monitoring the vital sign signals over an evaluation period; and
   classifying a sleep state of the subject based on results from monitoring the vital signs.

2. The method of claim 1, wherein the radar signal is a radar impulse signal.

3. The method of claim 2, wherein the radar signal is an ultra-wide band (UWB) radar impulse signal.

4. The method of claim 1, further comprising determining whether the subject has a sleep disorder based on classifying the sleep state.

5. The method of claim 1, wherein processing the RF response signal further comprises applying a circle fitting algorithm to the plurality of spatial channels to correct for direct current (DC) offset.

6. The method of claim 1, wherein processing the RF response signal further comprises identifying the one or more mixed respiratory and cardiac spatial channels based on phase rotation of the plurality of spatial channels.

7. The method of claim 6, wherein identifying the one or more mixed respiratory and cardiac spatial channels comprises identifying spatial channels having an expected phase rotation arc.

8. The method of claim 7, wherein processing the RF response signal further comprises identifying the one or more respiratory spatial channels from spatial channels having a phase rotation arc outside the expected phase rotation arc.

9. The method of claim 1, wherein extracting the cardiac signal from the mixed respiratory and cardiac spatial channel comprises:
   extracting the respiratory signal from the one or more respiratory spatial channels; and
   removing the respiratory signal from the one or more mixed respiratory and cardiac spatial channels.

10. The method of claim 9, wherein:
   the respiratory signal is extracted from a selected respiratory spatial channel of the one or more respiratory spatial channels; and
   the respiratory signal is removed from a selected mixed respiratory and cardiac spatial channel of the one or more mixed respiratory and cardiac spatial channels.

11. The method of claim 10, wherein the selected respiratory spatial channel and the selected mixed respiratory and cardiac spatial channel are selected based on which combination among the one or more respiratory spatial channels and the one or more mixed respiratory and cardiac spatial channels produces a higher signal to noise ratio (SNR).

12. The method of claim 1, wherein the radar signal comprises ultra-wide band (UWB) radar impulses having a bandwidth between 1.0 gigahertz (GHz) and 2.0 GHz.

13. The method of claim 1, wherein the evaluation period comprises a predicted sleep cycle of the subject.

14. The method of claim 1, further comprising monitoring vital signs of multiple subjects over the evaluation period.

* * * * *